United States Patent [19]

Tiedeken

[11] Patent Number: 4,996,977

[45] Date of Patent: Mar. 5, 1991

[54] TREMOR CONTROL DEVICE

[76] Inventor: Edwin T. Tiedeken, 104 Cromwell Crt., Woodbury, N.J. 08096

[21] Appl. No.: 357,165

[22] Filed: May 26, 1989

[51] Int. Cl.⁵ .................... A63B 23/12; A63B 23/16
[52] U.S. Cl. ................................ 128/77; 248/118; 272/144
[58] Field of Search ............... 248/118, 286; 128/877, 128/878, 77, 88; 297/411; 280/647, 657, 658, 304, 304.1

[56] References Cited

U.S. PATENT DOCUMENTS

| | | | |
|---|---|---|---|
| 1,516,795 | 11/1924 | Schwarting | 248/118 |
| 2,630,288 | 3/1953 | Eubanks | 248/125 |
| 3,124,328 | 3/1964 | Kortsch | 248/118 |
| 3,906,648 | 9/1975 | Bard | 38/102.2 |
| 3,929,309 | 12/1975 | De Voie | 248/118 |
| 4,237,873 | 12/1980 | Terry et al. | 128/77 |
| 4,259,949 | 4/1981 | Axelsson | 128/77 |
| 4,784,120 | 11/1988 | Thomas | 128/77 |

FOREIGN PATENT DOCUMENTS 62687 8/1944 Denmark.
42022 10/1965 German Democratic Rep..
112238 1/1918 United Kingdom.

Primary Examiner—Richard J. Apley
Assistant Examiner—Jerome Donnelly
Attorney, Agent, or Firm—Thomas A. Lennox

[57] ABSTRACT

A tremor control device is provided to control spastic movements of a person's forearm caused by cerebral palsy. The device is connected to a wheelchair or work station in front of the person by the interfitting of a horizontal travel support member into holes of an attachment device. A trolley rides along the travel support member capable of full rotational movement around the member. A forearm rest, which restrains the forearm in position is attached to a slide which slides in a lineal direction, the base support of which is connected to the trolley through an attachment that allows the full rotational movement in a plane perpendicular to that of the rotational movement of the trolley.

29 Claims, 3 Drawing Sheets

TREMOR CONTROL DEVICE

BACKGROUND OF THE INVENTION

This inventions involves a device to control involuntary tremors of a person's limb. More specifically, it involves a device to improve the manual dexterity and control of a person suffering from hand and arm tremors.

Persons having cerebral palsy and other motor disorder dysfunctions suffer from spastic involuntary muscle movements. The involuntary movements of the person's arms not only prevent the person from accomplishing menial tasks, such as eating, but also prevent the person from continuing a productive life due to the lack of control of the hand movement. Specifically, the tremors prevent the person from picking up food and guiding it to his or her mouth. The tasks of dialing a telephone or accurately striking a computer keyboard are made essentially impossible for the cerebral palsy victim. In these forms of neuro-motor disorders, willed movements of the arm in a particular direction and angle, are interfered with by the intermittent or continuous tremors of the limb and hand. An arm and hand brace support utilizing an articulated frame with a train of linked arms attached to a base member near the shoulder of the person has been provided. However, the strength needed to overcome the spring resistance and the substantial play of the articulated arm limit the effectiveness of the device. Another arm constraint offered as an aid for self-feeding of a person afflicted with tremors utilizes rotational movement in two planes, but the possible willed movement is too restricted for general use.

None of the prior devices provide effective dampening of involuntary arm spasms while allowing the versatility of willed movement in essentially any direction. The present invention answers these needs as well as attaining the objects described herein below.

SUMMARY OF THE INVENTION

It is an object of the present invention to provide a tremor control device to dampen and restrict involuntary movements of a person's hand and arm.

It is a specific object of the present invention to provide a tremor control device which is attachable on the front of the chair, wheelchair or work station in front of the person to aid in the use of the arm using the device to reach a target on the other side of the device.

It is an additional object of the present invention to provide a tremor control device that will attach on a horizontal bar spanning the arms of a wheelchair, allowing the person to strap his or her arm into the device and control the tremors while carrying out tasks in front of the person.

It is a specific object of the present invention to provide a dampening of involuntary arm spasms of a person attempting to accurately position the hand on a keyboard or touch-tone telephone.

It is an additional object of the present invention to provide a tremor control device that will move in any direction with essentially no resistance in achieving the willed movements and yet effectively dampen and control spastic movements.

It is a specific object of the present invention to provide a tremor control device that provides sturdy support sufficient to resist any forces applied to it by involuntary spasms and yet provide for unrestricted easy willed movement by the person's forearm.

It is an additional object of the present invention to provide a tremor control device that provides sturdy support to resist tremor forces, while capable of easy attachment and disattachment to and from in front of the person using the device.

It is a further object of the invention to provide a tremor control device that allows essentially free movement in a willed direction and yet tends to bind when tremor movement is not along the aligned direction of movable parts of the device.

The invention is a tremor control device to restrict involuntary tremors of a person's forearm. The device includes a travel support member having a lengthwise axis of alignment and a trolley means including a trolley member to travel along the lengthwise axis of the travel support member. The device further includes a slide support member and slide member interlocked to the slide support member restricting movement of the slide member along a line. The device further includes arm support means attached to the slide member to support the person's forearm and arm attachment means to restrain the forearm in the arm support means. The device further includes universal attachment means to attach the slide support member to the travel support member through the trolley means, wherein the attachment allows rotational movement of the slide support member in relation to the slide support member in two separate planes.

A preferred tremor control device includes a travel support member having a lengthwise axis of alignment and a trolley means including a trolley member to travel along the travel support member. The preferred device further includes trolley attachment means to attach the trolley means to the travel support member restricting movement of the trolley means to linear movement along a line parallel to the lengthwise axis of the travel support member, and rotational movement on a first plane perpendicular to the lengthwise axis of the travel support member. The preferred device also includes a slide support member and slide support member attachment means to attach the slide support member to the trolley means restricting movement of the slide support member attachment means to rotational movement on a second plane perpendicular to the first plane. The device further includes a slide member interlocked to the slide support member restricting movement of the slide member along a line parallel to the second plane, arm support means attached to the slide member to support the person's forearm, and arm attachment means to restrain the forearm in the arm support means.

It is preferred that the travel support member include a horizontal bar. It is also preferred that the device further include travel support member attachment means to attach the travel support member to a base frame in a position horizontally crosswise in front of the person. It is further preferred that the travel support member attachment means has the capability to attach the travel support member to the arms of a wheelchair. It is also preferred that the trolley attachment means include a trolley member with a round aperture of a size to interfit around the travel support member to slide freely along the length of the bar and allow the trolley member to rotate around the bar. It is further preferred that the slide support member include at least one truncated triangular cross-sectioned shaped groove and the slide member include a complimentary interlocking truncated triangular cross-sectioned shaped projection sized to allow free interlocked sliding of the slide member along the groove of the slide support member. It is also preferred that the device further include stop members to stop movement of the slide member to avoid disengagement of the projection from the groove in either direction. It is further preferred the line of movement of the slide member be parallel to the second plane. It is also preferred that the device further include a travel support member attachment means comprising members with upright openings of a size and shape to receive downward depending projections from the ends of the travel support member. It is further preferred that the material of and tolerances between opposing surfaces of the slide support member and the slide member be chosen to provide essentially free movement along the line, but bind to essentially prevent movement along any other line. It is further preferred that the material of and tolerances between opposing surfaces of the universal attachment means be chosen to provide essentially free movement along the second line and in the first and second planes, but bind to essentially prevent movement along any other line or in any other planes.

The invention is also a method of controlling involuntary tremors of a person's forearm while allowing unrestricted movement of the forearm. The method includes attaching a travel support member having a lengthwise axis of alignment in front of the person, and attaching trolley means onto the travel support member, the trolley means includes a trolley member to travel along the lengthwise axis of the travel support member. The method further includes attaching of the slide support member to the trolley means, wherein the attaching of the slide support member to the travel support member through the trolley means allows rotational movement of the slide support member in relation to the slide support member in two separate planes. The method also includes interlocking a slide member to the slide support member restricting movement of the slide member along a line. The method further includes attaching arm support means to the slide member to support the person's forearm, and restraining the forearm in the arm support means with arm attachment means.

It is preferred that the attaching of the slide support member to the travel support member through the trolley means include attaching the trolley means to the travel support member restricting movement of the trolley means to linear movement along a line parallel to the lengthwise axis of the travel support member, and rotational movement on a first plane perpendicular to the lengthwise axis of the travel support member, and that the attaching of the slide support member to the travel support member through the trolley means further include attaching the slide support member to the trolley means restricting movement of the slide support member attachment means to rotational movement on a second plane perpendicular to the first plane. It is further preferred that the method further include attaching the travel support member to a base frame in a position horizontally crosswise in front of the person. It is further preferred that the attaching the trolley means include providing the trolley member with a round aperture of a size to interfit around the travel support member to slide freely along the length of the bar and allow the trolley member to rotate around the bar. It is further preferred that the interlocking of the slide member into the slide support member include providing at least one truncated triangular cross-sectioned shaped groove in the slide support member and providing on the slide member a complimentary interlocking truncated triangular cross-sectioned shaped projection size to allow free interlocked sliding of the slide member along the groove of the slide support member. It is further preferred that the method further include providing stops to stop movement of the slide member to avoid disengagement of the projection from the groove in the slide support member in either direction.

DESCRIPTION OF PREFERRED EMBODIMENTS

Figure 1:
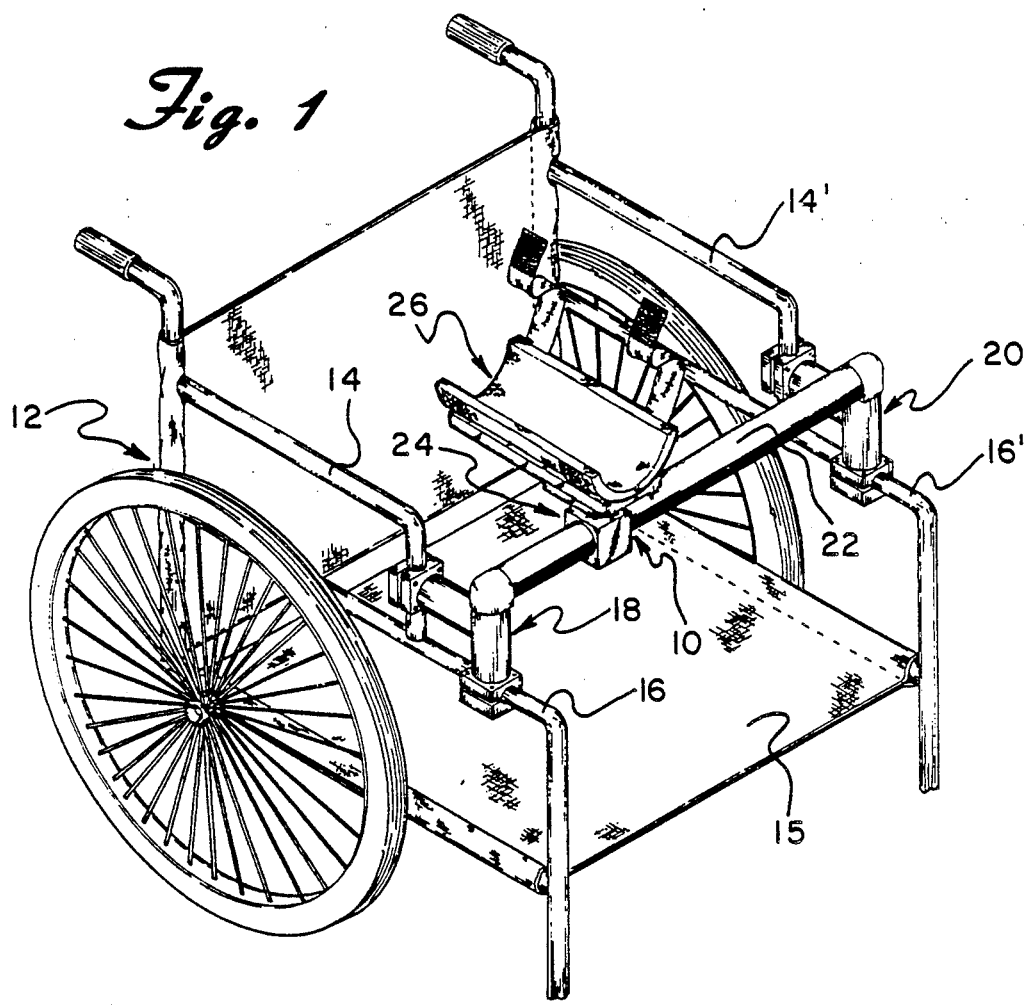
FIG. 1 is a perspective view of a tremor control device of the present invention attached to the arms of a wheelchair.

In FIG. 1, tremor control device 10 is attached to wheelchair 12. In this typical wheelchair construction, arm rest 14 extends along both sides of seat area 15. Support frames 16 are the basic frame structure of wheelchair 12 and include horizontal members to which "L" shaped arm rests 14 attach at their lower end. Right base attachment device 18 attaches to arm rest 14 and frame 16 on the right side of wheelchair 12 and left base attachment device 20 attaches to arm rest 14' and frame 16' on the left side of wheelchair 12. Travel support member 22 interconnects to attachment devices 18 and 20 spanning the distance between arm rests 14 and 14' in a horizontal position over and proximate the front of seat 15. Arm support device 26 interconnects and attaches to travel support member 22 through universal attachment device 24, mostly hidden in this view. Attachment devices 18 and 20, or duplicates thereof, may be attached to a work station. Then device 10 may lifted off the wheelchair and attached to the work station. Modifications of the device include providing attachment device to hold member 22 at an angle, such as upwardly toward the person's head. In this configuration the device is an effective aid in eating. In the configuration as illustrated, the natural flexing of frames 16 inwardly when the person sits on the wheelchair, tends to bind member 22 into attachment devices 18 and 20.

Figure 2:
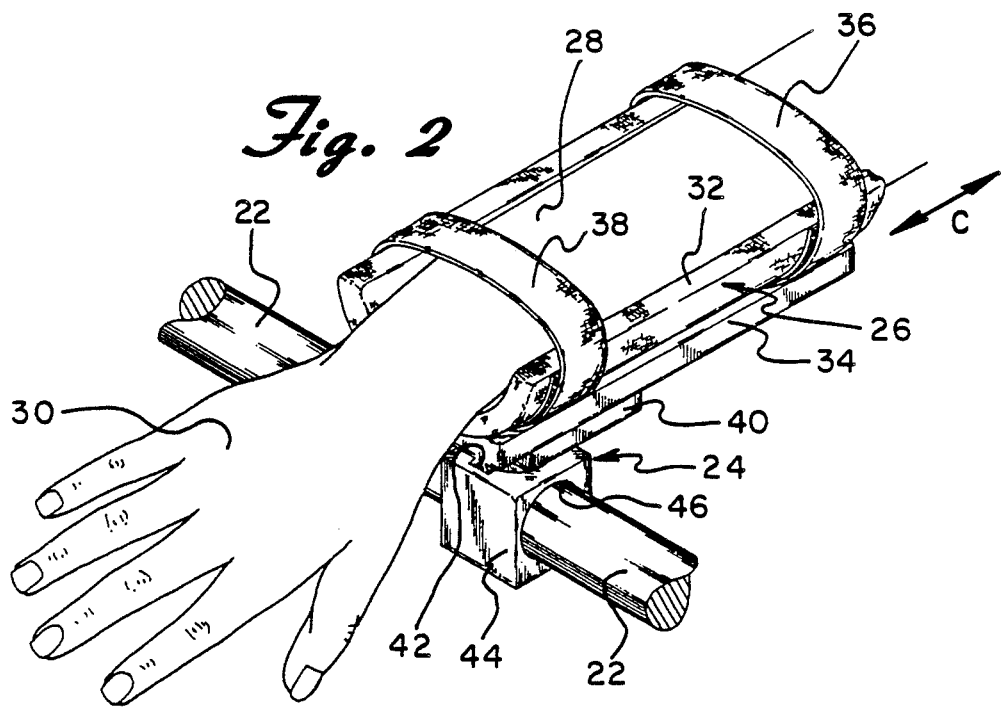
FIG. 2 is a perspective view of a portion of the tremor control device illustrated in FIG. 1 showing the person's arm strapped in position.

In FIG. 2, forearm 28 is shown in cradle shape forearm rest 32 with hand 30 extending outwardly frontwardly from the device. Forearm rest 32 is a semi-cylindrical shape cut lengthwise to form a trough of cloth/foam covered polymeric plastic rigid thermo-plastic structure capable of firmly yet comfortably restraining forearm 28 in position. Cloth straps 36 and 38 are permanently attached at one end to a lengthwise side of forearm rest 32 extending over the top of the shape opening and attaching with VELCRO® hook and loop fabric fastener switches on the other lengthwise side firmly holding forearm 28 in place. This combination structure of arm support device 26 essentially prevents movement of the forearm without movement of some portion of device 10. Forearm rest 32 is structurally attached to slide member 34 which is a flat rectangular aluminum base panel with lengthwise interlocking projections 42 depending from the bottom surface. Projection 32 (and 32' hidden in this view) interlocks and slides in a slide support member 40 which is attached through universal attachment device 24 to a trolley 44 which slides along the length of travel support member 22. Device 24 includes the attachment mechanisms between arm support device 26 and rod 22, the movements of device 24 being illustrated in FIGS. 6 and 7. Trolley 44 is a solid aluminum member having a circular hole 46 of a size to interfit around travel support 22 and slide freely along its length. Although not shown, trolley 44 may be constructed of two parts to allow attachment on member 22.

The interlocking of trolley 44 onto travel support member 22 with round hole 46 allows trolley 44 not only to slide lengthwise, but to rotate around member 22 in any position in a plane that in this embodiment is vertical and perpendicular with the lengthwise axis of travel support member 22. This connection and movement is part of universal attachment means 24 between trolley 44 and the slide support member 40.

Figure 3:
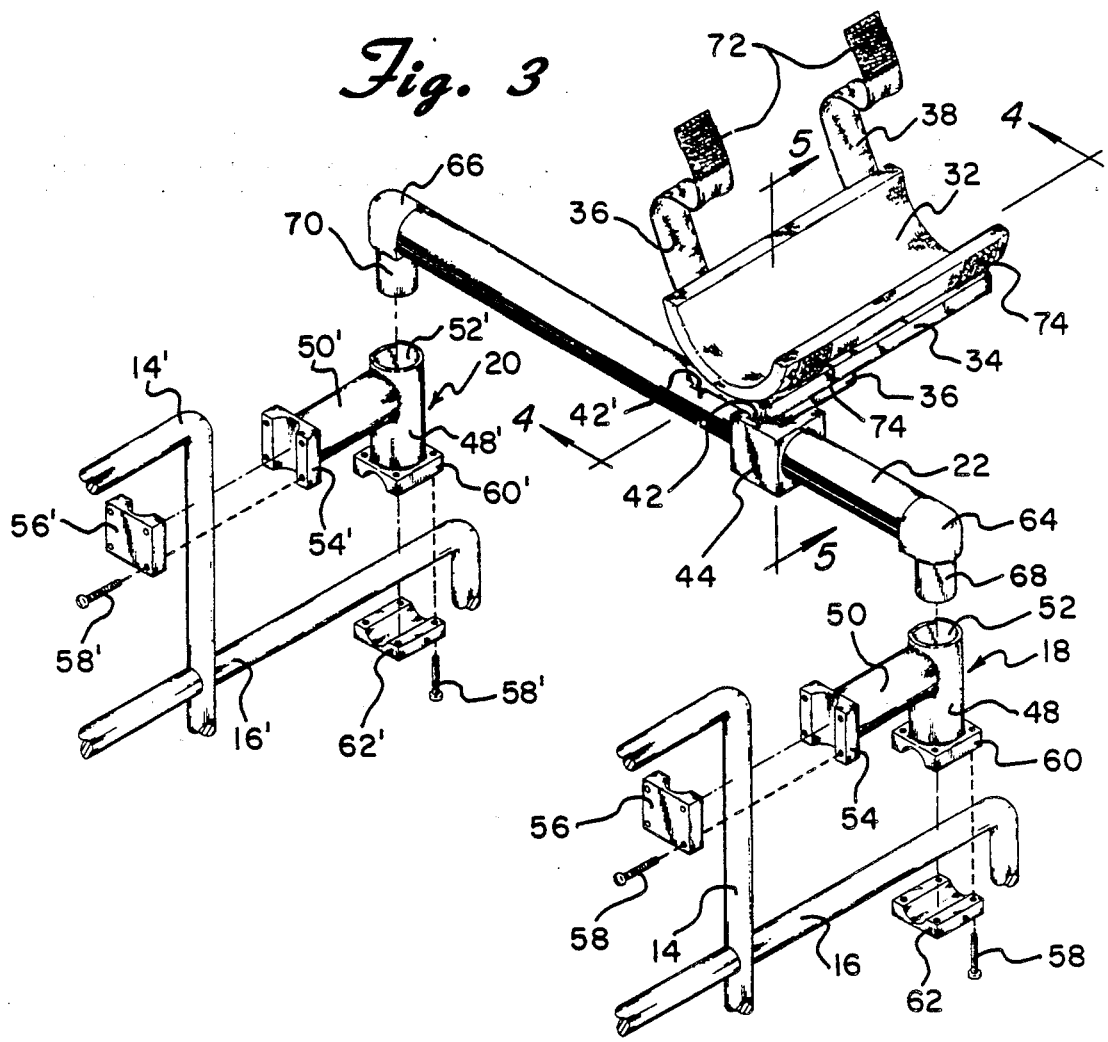
FIG. 3 is an exploded perspective view of the tremor control device illustrated in FIG. 1 showing attachment of the device to the wheelchair arms.

In FIG. 3, the exploded drawing illustrates how right base attachment device 18 and left base attachment device 20 attach and interconnect to arm rests 14 and 14' and support frames 16 and 16' of the wheelchair. Since attachment devices 18 and 20 are essentially identical, the corresponding equivalent parts are numbered identically with each part number of device 20 having a "'" added thereto. For the purposes of avoiding repetition, only right base attachment device 18 will be described with a description of device 20 being identical except for the inclusion of the "'" on each number. Device 20 includes an "L" shaped attachment device constructed of cylindrical aluminum tubing with horizontal connector 50 welded to the side of upright connector 48. This leaves circular opening end 52 of connector 48 free and clear. Welded on the exposed end of horizontal connector 50 is attachment clamp member 54 which includes a semi-cylindrical concave surface vertically positioned to interfit onto the outside surface of the cylindrical tube shape of arm rest 14. Free attachment clamp 56 is a machined aluminum member with a matching vertical concave cylindrical shape to match and interfit over arm rest 14. Attachment clamp 54 is placed against arm rest 14 and mated with free attachment clamp 56 to essentially completely surround arm rest 14. Machine bolts 58 extend through horizontal holes in clamp 56 into threaded holes of attachment clamp 54 to hold the parts together and securely fasten them around arm rest 14. Horizontal attachment clamp 60 is attached on the bottom end of vertical connector 48 having a shape similar to that of attachment clamp 54 except that the cylindrical concave shape is positioned horizontally to mate with and partially surround support frame 16. Free horizontal attachment clamp 62 is similar in shape to clamp 56 and is connected with bolts 58 in the same fashion around support frame 16 to horizontal attachment clamp 60. In a similar fashion, left base attachment device 20 is attached to arm rest 14' and support frame 16'. When in place, attachment device 18 and 20 are securely fastened to wheelchair 12 providing vertical round openings 52 and 52' opening upwardly. At the ends of travel support member 22 are integral right elbow shape 64 integral and left elbow shape 66, each providing a stop for trolley 44 at each end of member 22 as well as turning and depending in a downward direction. Right vertical projection 68 is a circular rod shape extending vertically downwardly from right elbow shape 64. Left vertical projection 70 also has a horizontal circular cross sectional shape and extends downwardly from left elbow shape 66. Projection 68 interfits and is inserted into end opening 52 while left vertical projection 70 extends downwardly and is inserted into end opening 52' with the sizes chosen for little play. In this configuration, travel support member 22 and all of the mechanism attached to trolley 44 are sturdily attached to wheelchair 12, but are easily removed by merely lifting upwardly on travel support member 22 to disengage projections 68 and 70 from holes 52 and 52'. In use, there is almost always a downward force on forearm rest 32 and thus downwardly on travel support member 22, so there is essentially no risk of inadvertently disconnecting support member 22 from attachment devices 18 and 20. In this view, VELCRO® hook fabric fastener strips 72 on the ends of straps 36 and 38 are shown disattached from VELCRO® loop fabric attachment strips 74, which are positioned on the outside surface of forearm rest 32 for attachment with the ends of straps 36 and 38.

Figure 4:
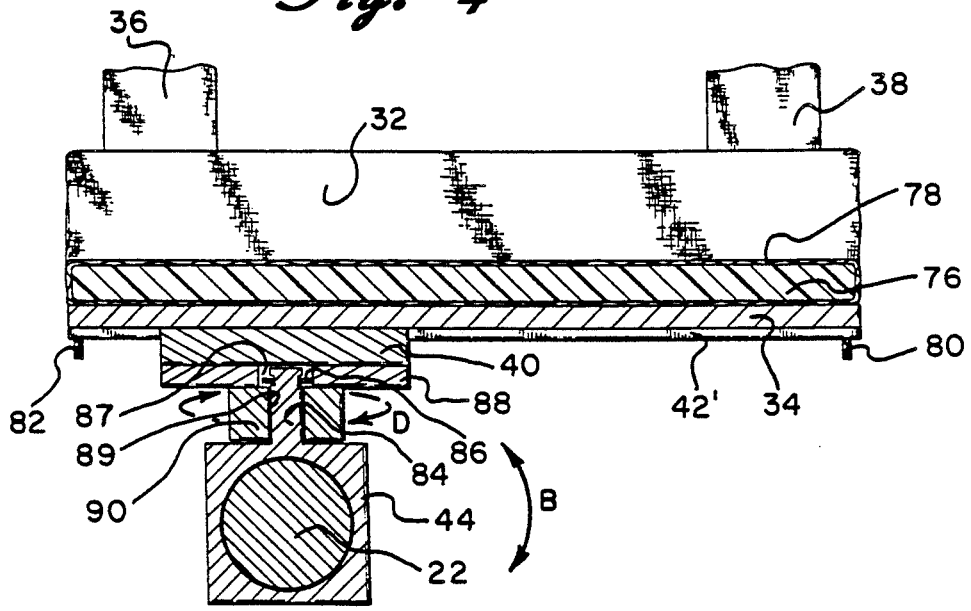
FIG. 4 is a cross-sectional view taken along lines 4—4 of FIG. 3.

In FIG. 4, construction of forearm rest 32 is illustrated of flexible rigid plastic shape 76 covered with soft cushioned cloth 78. The length of interlocking projection 42', a soft flexible foam panel, may be included under cloth 78 over shape 76, which is identical to that of projection 42, except that projection 42' projects downwardly along one edge, while projection 42 projects downwardly along the other lengthwise edge of slide member 34. Front stop member 80 prevents slide member 34 from disengaging from interlocking slots in slide support member 40 while rear stop member 82 prevents slide member 34 from disengaging from the interlocking slots of slide support member 40 to the front. The interconnection between slide support member 40 and trolley 44 is important in that it provides full rotational movement of the upper structure essentially perpendicular to that of the rotational plane of trolley 44 around support member 22. The rotation of this interconnection is horizontal in this view. Although this can be accomplished in a variety of mechanisms, vertical circular rod 84 is an integral part of trolley 44 extending upwardly to approach slide support member 40. Base member 88 is attached to the bottom of slide support member 40 and provide an opening to seat locking ring 86 which when held in place by locking member 90 prevents rod 84 from dropping downwardly, while allowing it to rotate freely in a horizontal plane. Hole 87 in slide support member 40 is large enough to receive locking ring 86, while hole 89 receives rod 84 is small enough to prevent ring 86 from dropping down. This holds rod 84 in place vertically.

Figure 5:
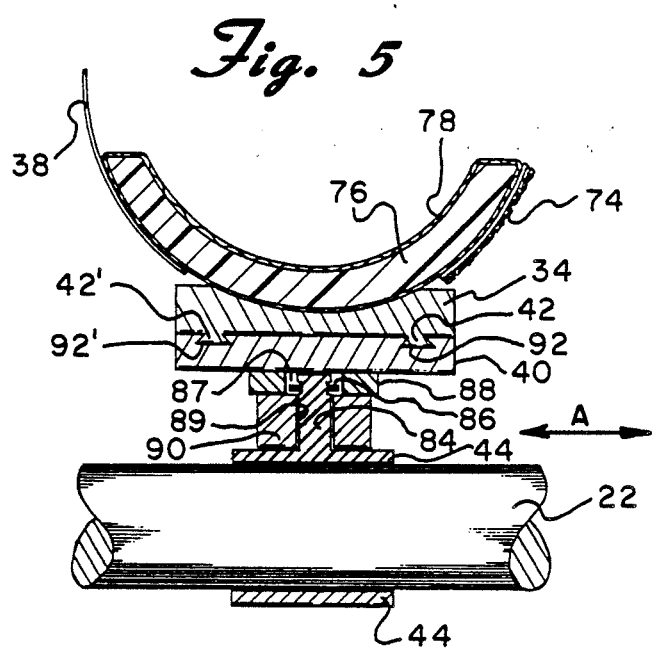
FIG. 5 is a cross-sectional view taken along lines 5—5 of FIG. 3.

In FIG. 5, the interlocking sliding relationship between slide member 34 and slide support member 40 is illustrated. Integral lengthwise projections 42 and 42' extend downwardly from the bottom surface of slide member 34. Projections 42 and 42' have a cross-section of a dove-tail shape of a truncated triangular with the widest portion facing downwardly. Slide support member 40 has matching complementary slots 92 and 92' which are dove-tail shaped with a cross-section of a truncated triangular shape, again with the wide portion downwardly. When projections 42 and 42' are interlocked into slide 92 and 92', slot member 34 freely slides along its entire length interlocked into slide support member 40. However, this construction essentially prevents any movement between the two interlocked parts other than lineal. All of the mating and sliding surfaces are metal to metal, and specifically aluminum to aluminum. The tolerances are chosen to allow free movement with little play. The surfaces and tolerances are chosen to allow essentially free movement, sliding or rotational, in the willed direction, but yet quick essentially immovable binding when uncontrollable movement occurs in a direction not aligned with the designed movement of the part. For example, the size and materials chosen for member 22 and hole 46 allow free sliding along the axis of alignment as long as the willed movement is very close to the axis. However, uncontrolled movement a direction only a few degrees away from the axis causes trolley 44 to bind and not move significantly, thus dampening the movement caused by the spasm. Likewise, the tolerances, shape, and materials chosen for slide member 34 and slide support member 40 allow free willed movement along a single line, but the dove-tailed interconnect binds if the spasm causes movement along any direction other than the single designed line.

Figure 6:
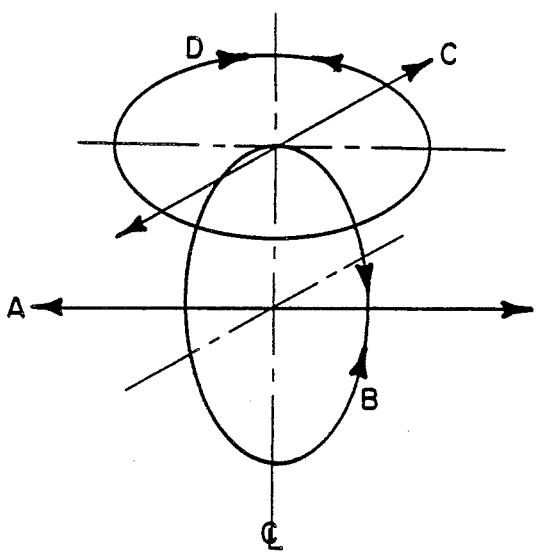
FIG. 6 is a diagram illustrating the relational movements of the tremor control device shown in the above figures.

FIG. 6 illustrates the relative movement of the components of device 10 and specifically that of universal attachment device 24. Lengthwise axis A of travel support member 22 is depicted herein in a horizontal position in the same fashion that travel support member 22 is positioned on the wheelchair in a horizontal position. It should be readily seen that this lengthwise axis may be at an angle and may even be in a vertical position depending upon the preferred movement and support configurations desired. However, the preferred alignment is in a horizontal position as it requires the least force to move the mechanism along the length of travel support member 22 and is most useful in front of the person using the device. The center line marked "C/L" indicates the vertical center line of trolley 44 and more specifically that of vertical circular rod 84. Circular rotational movement of trolley 44 is depicted by circular arrows "B" indicating that the trolley can be rotated to any position around support member 22. Rotational movement of the attachment between slide support member 40 and trolley 44 is depicted by circular arrows "D", which, when slide member 34 is a horizontal position, the plane of rotation depicted by arrows "D" is also in a horizontal position. The combination of movements "B" and "D" constitute the movement of universal attachment device 24. Arrows "C" depict the sliding lineal movement of slide member 34 along slide support member 40. That sliding lineal movement is shown here in the same plane as rotational movement "D", although it should be understood that that sliding movement is, from a practical standpoint, along a line that is parallel to the plane of movement "D".

Figure 7:
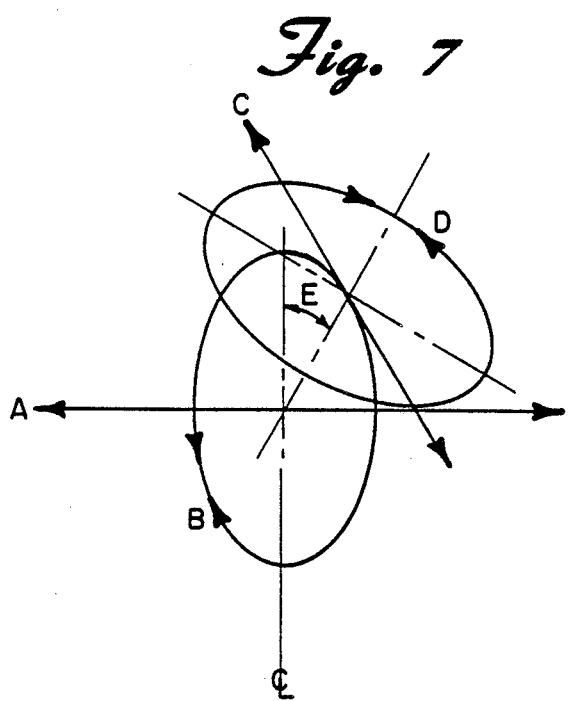
FIG. 7 is a diagram illustrating additional movement capabilities of the tremor control device in the above figures.

As suggested above, it would be wrong to picture plane "D" as always in a horizontal position and the diagram of FIG. 7 illustrates the versatility of movement. As trolley 44 is rotated around in plane "B" through angle "E" lineal movement "C" of slide member 34 is now changed such that its movement is no longer horizontal but, as illustrated here is pointed downwardly to the front and upwardly to the rear. At the same time, rotational plane "D", that being of the rotational movement of the interconnection between member 40 and trolley 44 is also tilted at an angle from horizontal. Thus, it should be apparent that with the two rotational movements, coupled with the lineal movement of trolley 44, the lineal sliding movement of slide member 34 may be positioned to move along any chosen lineal line. Thus, with a little practice, the person can actually move the forearm and thus the hand directly toward any chosen target. Since by their very uncontrolled nature, tremors do not operate along a single lineal line and thus are dampened or essentially prevented from affecting the movement toward a particular target.

While this invention has been described with reference to the specific embodiments disclosed herein, it is not confined to the details set forth and the patent is intended to include modifications and changes which may come within and extend from the following claims.

I claim:

1. A tremor control device to control involuntary tremors of a person's forearm comprising:
   (a) a travel support member having a lengthwise axis of alignment,
   (b) trolley means comprising a trolley member to travel along the lengthwise axis of the travel support member,
   (c) a slide support member,
   (d) a slide member interlocked to the slide support member restricting movement of the slide member along a line,
   (e) arm support means attached to the slide member to support the person's forearm,
   (f) arm attachment means to restrain the forearm in the arm support means, and
   (g) universal attachment means to attach the slide support member to the travel support member through the trolley means, wherein the attachment allows rotational movement of the slide support member in relation to the travel support member in two separate planes.

2. The device of claim 1 wherein the universal attachment means comprises:
   (a) trolley attachment means to attach the trolley means to the travel support member restricting movement of the trolley means to:
      (i) linear movement along a second line parallel to the lengthwise axis of the travel support member, and
      (ii) rotational movement on a first plane perpendicular to the lengthwise axis of the travel support member, and
   (b) slide support member attachment means to attach the slide support member to the trolley means restricting movement of the slide support member attachment means to rotational movement on a second plane perpendicular to the first plane.

3. The device of claim 1 wherein the travel support member comprises a horizontal bar.

4. The device of claim 1 wherein the device further comprises travel support member attachment means to attach the travel support member to a base frame in a position horizontally crosswise in front of the person.

5. The device of claim 4 wherein the travel support member attachment means has the capability to attach the travel support member to the arms of a wheelchair.

6. The device of claim 2 wherein the trolley attachment means comprises a trolley member with an round aperture of a size to interfit around the travel support member to slide freely along the length of the bar and allow the trolley member to rotate around the bar.

7. The device of claim 1 wherein the slide support member comprises at least one truncated triangular cross-sectioned shaped groove and the slide member comprises a complimentary interlocking truncated triangular cross-sectioned shaped projection sized to allow free interlocked sliding of the slide member along the groove of the slide support member.

8. The device of claim 7 wherein the device further comprises stops to stop movement of the slide member to avoid disengagement of the projection from the groove in either direction.

9. The device of claim 2 wherein the line of movement of the slide member is parallel to the second plane.

10. The device of claim 1 wherein the device further comprises a travel support member attachment means comprising members with upright openings of a size and shape to receive downward depending projections from the ends of the travel support member.

11. The device of claim 1 wherein the material of and tolerances between opposing surfaces of the slide support member and the slide member are chosen to provide essentially free movement along the line, but bind to essentially prevent movement along any other line.

12. The device of claim 2 wherein the material of and tolerances between opposing surfaces of the universal attachment means are chosen to provide essentially free movement along the second line and in the first and second planes, but bind to essentially prevent movement along any other line or in any other planes.

13. A tremor control device to control involuntary tremors of a person's forearm comprising:
 (a) a travel support member having a lengthwise axis of alignment,
 (b) trolley means comprising a trolley member to travel along the travel support member,
 (c) trolley attachment means to attach the trolley means to the travel support member restricting movement of the trolley means to:
  (i) linear movement along a second line parallel to the lengthwise axis of the travel support member, and
  (ii) rotational movement on a first plane perpendicular to the lengthwise axis of the travel support member,
 (d) a slide support member,
 (e) slide support member attachment means to attach the slide support member to the trolley means restricting movement of the slide support member attachment means to rotational movement on a second plane perpendicular to the first plane,
 (f) a slide member interlocked to the slide support member restricting movement of the slide member along a first line parallel to the second plane,
 (g) arm support means attached to the slide member to support the person's forearm, and
 (h) arm attachment means to firmly hold the forearm in the arm support means.

14. The device of claim 13 wherein the travel support member comprises a horizontal bar.

15. The device of claim 13 wherein the device further comprises travel support member attachment means to attach the travel support member to a base frame in a position horizontally crosswise in front of the person.

16. The device of claim 13 wherein the trolley attachment means comprises a trolley member with a round aperture of a size to interfit around the travel support member to slide freely along the length of the bar and allow the trolley member to rotate around the bar.

17. The device of claim 13 wherein the slide support member comprises at least one truncated triangular cross-sectioned shaped groove and the slide member comprises a complimentary interlocking truncated triangular cross-sectioned shaped projection sized to allow free interlocked sliding of the slide member along the groove of the slide support member.

18. The device of claim 13 wherein the device further comprises a travel support member attachment means comprising members with upright openings of a size and shape to receive downward depending projections from the ends of the travel support member.

19. The device of claim 13 wherein the material of and tolerances between opposing surfaces of the slide support member and the slide member are chosen to provide essentially free movement along the line, but bind to essentially prevent movement along any other line.

20. The device of claim 13 wherein the material of and tolerances between opposing surfaces of the universal attachment means are chosen to provide essentially free movement along the second line and in the first and second planes, but bind to essentially prevent movement along any other line or in any other planes.

21. A method of controlling involuntary tremors of a person's forearm while allowing unrestricted movement of the forearm, the method comprising:
 (a) attaching a travel support member having a lengthwise axis of alignment in front of the person,
 (b) attaching trolley means onto the travel support member, the trolley means comprising a trolley member to travel along the lengthwise axis of the travel support member,
 (c) attaching a slide support member to the trolley means,
 wherein the attaching of the slide support member to the travel support member through the trolley means allows rotational movement of the slide support member in relation to the travel support member in two separate planes,
 (d) interlocking a slide member to the slide support member restricting movement of the slide member along a line,
 (e) attaching arm support means to the slide member to support the person's forearm, and
 (f) restraining the forearm in the arm support means with arm attachment means.

22. The method of claim 21 wherein attaching of the slide support member to the travel support member through the trolley means comprises:
 (a) attaching the trolley means to the travel support member restricting movement of the trolley means to:
  (i) linear movement along a second line parallel to the lengthwise axis of the travel support member, and
  (ii) rotational movement on a first plane perpendicular to the lengthwise axis of the travel support member, and
 (e) attaching the slide support member to the trolley means restricting movement of the slide support member attachment means to rotational movement on a second plane perpendicular to the first plane.

23. The method of claim 21 wherein the method further comrprises attaching the travel support member to a base frame in a position horizontally crosswise in front of the person.

24. The method of claim 23 wherein the attaching of the travel support member is to the arms of a wheelchair.

25. The method of claim 22 wherein attaching the trolley means comprises providing the trolley member with an round aperture of a size to interfit around the travel support member to slide freely along the length of the bar and allow the trolley member to rotate around the bar.

26. The method of claim 21 wherein the interlocking of the slide member into the slide support member comprises providing at least one truncated triangular cross-sectioned shaped groove in the slide support member and providing on the slide member a complimentary interlocking truncated triangular cross-sectioned shaped projection sized to allow free interlocked sliding of the slide member along the groove of the slide support member.

27. The method of claim 21 wherein the method further comprises attaching the travel support member to members of an attachment means comprising with upright openings of a size and shape to receive downward depending projections from the ends of the travel support member.

28. The method of claim 21 wherein the material of and tolerances between opposing surfaces of the slide support member and the slide member are chosen to provide essentially free movement along the line, but bind to essentially prevent movement along any other line.

29. The method of claim 22 wherein the material of and tolerances between opposing surfaces of the trolley means, travel support member, and the slide support member are chosen to provide essentially free movement along the second line and in the first and second planes, but bind to essentially prevent movement along any other line or in any other planes.

* * * * *